US010441590B2

(12) United States Patent
Bhat et al.

(10) Patent No.: US 10,441,590 B2
(45) Date of Patent: Oct. 15, 2019

(54) METHODS FOR TREATING PULMONARY HYPERTENSION

(71) Applicant: Reviva Pharmaceuticals, Inc., Santa Clara, CA (US)

(72) Inventors: Laxminarayan Bhat, Santa Clara, CA (US); Marc Cantillon, Santa Clara, CA (US); Ellen M. Wallis, Santa Clara, CA (US); Seema Rani Bhat, Santa Clara, CA (US)

(73) Assignee: Reviva Pharmaceuticals, Inc., Cupertino, CA (US)

( * ) Notice: Subject to any disclaimer, the term of this patent is extended or adjusted under 35 U.S.C. 154(b) by 0 days.

(21) Appl. No.: 15/643,630

(22) Filed: Jul. 7, 2017

(65) Prior Publication Data

US 2018/0125851 A1 May 10, 2018

Related U.S. Application Data

(63) Continuation of application No. PCT/US2016/012873, filed on Jan. 11, 2016.

(60) Provisional application No. 62/102,470, filed on Jan. 12, 2015.

(51) Int. Cl.
*A61K 31/538* (2006.01)
*A61P 9/12* (2006.01)
*A61P 25/24* (2006.01)
*A61P 25/22* (2006.01)

(52) U.S. Cl.
CPC .......... *A61K 31/538* (2013.01); *A61P 9/12* (2018.01); *A61P 25/22* (2018.01); *A61P 25/24* (2018.01)

(58) Field of Classification Search
None
See application file for complete search history.

(56) References Cited

U.S. PATENT DOCUMENTS

| 4,613,598 A | 9/1986 | Fukami et al. |
|---|---|---|
| 8,247,420 B2 | 8/2012 | Bhat et al. |
| 2008/0312249 A1 | 12/2008 | Chen |
| 2009/0298819 A1 | 12/2009 | Bhat |
| 2010/0216783 A1* | 8/2010 | Bhat ............ A61K 31/538 514/230.5 |
| 2017/0035772 A1 | 2/2017 | Bhat |

FOREIGN PATENT DOCUMENTS

| WO | 2004/046124 A1 | 6/2004 |
|---|---|---|
| WO | 2006/072608 A2 | 7/2006 |
| WO | 2008/047883 A1 | 4/2008 |
| WO | 2010/099502 A1 | 9/2010 |
| WO | 2015/131856 A1 | 9/2015 |
| WO | 2015/157451 A1 | 10/2015 |

OTHER PUBLICATIONS

Hironaka et al. In Cardiovascular Research 60, 692-699 (2003) (Year: 2003).*
Tomic et al. In Bioorganic and Medicinal Chemistry Letters 14, 4263-4266 (2004) (Year: 2004).*
Ghofrani et al (Meeting Abstract, American Thoracic Society Journals, 2012) (Year: 2012).*
International Search Report dated May 17, 2016 of PCT/2016/012873 (5 pages).
Reviva Pharmaceuticals Announces Successful End-of-Phase 2 Meeting With FDA for RP5063—Business Wire (Nov. 5, 2013), 4 pages.
Marcos E et al: "Serotonin Transporter Inhibitors Protect Against Hypoxic Pulmonary Hypertension", American Journal of Respiratory and Critical Care Medicine, American Lung Association, New York, NY, US, vol. 168, No. 4, Aug. 15, 2003 (Aug. 15, 2003), pp. 487-493.
E Hironaka: "Serotonin receptor antagonist inhibits monocrotaline-induced pulmonary hypertension and prolongs survival in rats", Cardiovascular Research, vol. 60, No. 3, Dec. 1, 2003 (Dec. 1, 2003), pp. 692-699.
Tomia M et al: "Pharmacological evaluation of selected arylpiperazines with atypical antipsychotic potential", Bioorganic & Medicinal Chemistry Letters, Pergamon, Amsterdam, NL, vol. 14, No. 16, Aug. 16, 2004 (Aug. 16, 2004), pp. 4263-4266.
Zhang Erquan et al: "Sarpogrelate hydrochloride, a serotonin 5HT2A receptor antagonist, ameliorates the development of chronic hypoxic pulmonary hypertension in rats", Journal of Anesthesia, Japan Society of Anesthesiology, Tokyo, JP, vol. 29, No. 5, May 1, 2015 (May 1, 2015), pp. 715-723.
European Search Report dated Jul. 27, 2018 for European Patent Application No. 16737674.8.

* cited by examiner

*Primary Examiner* — Dennis Heyer
(74) *Attorney, Agent, or Firm* — Perkins Coie LLP; Viola T. Kung

(57) ABSTRACT

The present invention provides a method of using arylpiperazine derivatives for treating pulmonary hypertension. The method comprises a step of administering to a patient in need thereof an effective amount of a compound of Formula 1, which is an arylpiperazine derivative.

10 Claims, No Drawings

METHODS FOR TREATING PULMONARY HYPERTENSION

This application is a continuation of PCT/US2016/012873, filed Jan. 11, 2016; which claims the priority of U.S. Provisional Application No. 62/102,470, filed Jan. 12, 2015. The contents of the above-identified applications are incorporated herein by reference in their entireties.

TECHNICAL FIELD

The present invention relates to methods of utilizing arylpiperazine derivatives for treating pulmonary hypertension.

BACKGROUND

Pulmonary hypertension summarizes various conditions in which the blood pressure in the pulmonary circulation is significantly elevated. By definition, pulmonary hypertension is diagnosed when the mean pulmonary arterial pressure (mPAP) exceeds 25 mmHg as measured by right-heart catheterization. Pulmonary arterial hypertension (PAH) is a syndrome in which pulmonary arterial obstruction increases pulmonary vascular resistance, which leads to right ventricular (RV) failure. Pulmonary hypertension is a serious illness that becomes progressively worse and is sometimes fatal. There are 5 categories of pulmonary hypertension (PH) in the latest World Health Organization classification: (1) PAH; (2) PH associated with left-sided heart disease; (3) PH associated with lung disease/hypoxia; (4) thromboembolic PH; and (5) miscellaneous. In all groups, the average pressure in the pulmonary arteries is higher than 25 mmHg at rest or 30 mmHg during physical activity, with a mean pulmonary-capillary wedge pressure and left ventricular end-diastolic pressure of less than 15 mmHg. The pressure in normal pulmonary arteries is 8-20 mmHg at rest. (The mmHg is millimeters of mercury—the units used to measure blood pressure.). There is no cure for PAH but treatments currently available can help lessen symptoms and improve your quality of life. Treatment of PAH involves the use of prostanoids (given intravenously, by inhalation, subcutaneously, or orally), endothelin receptor blockers, and PDE5 inhibitors. PAH treatments remain expensive and/or difficult to deliver and are more palliative than curative.

Although many advances have been made in recent years, especially pertaining to the molecular genetics and cell biology of idiopathic pulmonary hypertension, the pathogenesis of most forms of PAH is still not fully understood. Serotonin or 5-Hydroxytryptamine (5-HT) has been reported to play a key role in both proliferative and functional components of PAH pathogenesis (Esteve et al., Cell Biochem Biophys 2007; Dempsie and MacLean, Brit j Pharmacol 2008; Dumitrascu et al., Eur Respir J 2011). Serotonin is a vasoconstrictor that promotes smooth-muscle cell hypertrophy and hyperplasia. Elevated levels of plasma serotonin and reduced content of serotonin in platelets have been found in idiopathic pulmonary hypertension. A platelet defect that defect that results in a reduced uptake of serotonin has been associated with PAH. Recently, mutations in the serotonin transporter (5-HTT), serotonin 2A receptor (5-HT2A) and serotonin receptor (5-HT2B) have been implicated in PAH (Eddahibi et al., J Clin Invest 2001). The 5-HT2A receptor present in human pulmonary arteries mediates vasoconstriction of the systemic circulation. Antagonism of the 5-HT2A receptor inhibits monocrotoline induced PAH in mice (Hironaka et al., Cardiovasc Res 2003), and also inhibits serotonin-induced pulmonary vasoconstriction in vessels from both normoxic and hypoxic rats (Morcroft et al., J Pharmacol Exp Ther 2005; Cogolludo et al., Circ Res 2006). Moreover, the 5-HT2A receptor mediates serotonin-induced proliferation of rat pulmonary arterial fibroblasts (Welsh et al., Am J Respir Crit Care Med 2004). 5-HT2B receptor is expressed in pulmonary endothelial and smooth muscle cells and stimulate calcium release in human endothelial cells from the pulmonary artery ((Esteve et al., Cell Biochem Biophys 2007). In the chronic hypoxic mouse model of pulmonary hypertension, researchers demonstrated that 5-HT2B receptor is involved in the development of pulmonary hypertension by mediating chronic hypoxic responses in wild-type mice compared with the complete absence of pulmonary hypertension and vascular remodeling in 5-HT2B receptor deficient mice (Launay et al., Nat Med 2002). Recently, PRX-08066, a selective 5-HT2B receptor antagonist (Provasnik et al., J Pharmacol Exp Ther 2010), and terguride, an antagonist of both 5-HT2A and 5-HTB receptors (Dumitrascu et al., Eur Respir 2011), were shown to prevent the development of PAH in rat monocrotoline (MCT) model. The pathogenesis of pulmonary hypertension is characterized by three major processes including vasoconstriction, vascular remodeling and microthrombotic events. In addition, accumulating evidence point to a cytokine driven inflammatory process as a major contributor to the development of pulmonary hypertension.

There is a pressing need for less expensive and more effective therapies for treating PAH.

DETAILED DESCRIPTION OF THE INVENTION

Definitions

"Alkyl" or "alkanyl" refers to a saturated, branched or straight-chain or cyclic monovalent hydrocarbon radical derived by the removal of one hydrogen atom from a single carbon atom of a parent alkane. Typical alkyl groups include, but are not limited to methyl; ethyl; propyls such as propan-1-yl, propan-2yl, cyclopropan-1-yl; butyls such as butan-1-yl, butan-2-yl, 2-methyl-propan-1-yl, 2-methyl-propan-2-yl, cyclobutan-1-yl and the like. Preferably, an alkyl group comprises from 1-20 carbon atoms, more preferably, from 1 to 10, or 1 to 6, or 1-4 carbon atoms.

"Alkenyl" refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl, cycloprop-2-en-1-yl; butenyls such as but-1-en-1-yl, but-1-en-2-yl, 2-methy-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien 1-yl, etc.; and the like.

"Alkynyl" refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn3-yl, but-3-yn-1-yl, etc.; and the like.

"Acyl" refers to a radical —C(O)R, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to formyl, acetyl, cyclohexylcarbonyl, cyclohexylmethylcarbonyl, benzoyl, benzylcarbonyl and the like.

"Acyloxyalkyloxycarbonyl" refers to a radical —C(O)OCR'R"OC(O)R"', where R', R", and R"' are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —C(O)OCH$_2$OC(O)CH$_3$, —C(O)OCH$_2$OC(O)CH$_2$CH$_3$, —C(O)OCH(CH$_3$)OC(O)CH$_2$CH$_3$, —C(O)OCH(CH$_3$)OC(O)C$_6$H$_5$ and the like.

"Acylalkyloxycarbonyl" refers to a radical —C(O)OCR'R"C(O)R"', where R', R", and R"' are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —C(O)OCH$_2$C(O)CH$_3$, —C(O)OCH$_2$C(O)CH$_2$CH$_3$, —C(O)OCH(CH$_3$)C(O)CH$_2$CH$_3$, —C(O)OCH(CH$_3$)C(O)C$_6$H$_5$ and the like.

"Acyloxyalkyloxycarbonylamino" refers to a radical —NRC(O)OCR'R"OC(O)R"', where R, R', R", and R"' are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —NHC(O)OCH$_2$OC(O)CH$_3$, —NHC(O)OCH$_2$OC(O)CH$_2$CH$_3$, —NHC(O)OCH(CH$_3$)OC(O)CH$_2$CH$_3$, —NHC(O)OCH(CH$_3$)OC(O)C$_6$H$_5$ and the like.

"Acylalkyloxycarbonylamino" refers to a radical —NRC(O)OCR'R"C(O)R"', where R, R', R", and R"' are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —NHC(O)OCH$_2$C(O)CH$_3$, —NHC(O)OCH$_2$C(O)CH$_2$CH$_3$, —NHC(O)OCH(CH$_3$)C(O)CH$_2$CH$_3$, —NHC(O)OCH(CH$_3$)C(O)C$_6$H$_5$ and the like.

"Acylamino" refers to "amide" as defined herein.

"Alkylamino" means a radical —NHR where R represents an alkyl, or cycloalkyl group as defined herein that may be optionally substituted by one or more substituents as defined herein. Representative examples include, but are not limited to, methylamino, ethylamino, 1-methylethylamino, cyclohexylamino and the like.

"Alkoxy" refers to a radical —OR where R represents an alkyl, or cycloalkyl group as defined herein that may be optionally substituted by one or more substituents as defined herein.

Representative examples include, but are not limited to methoxy, ethoxy, propoxy, butoxy, cyclohexyloxy and the like.

"Alkoxycarbonyl" refers to a radical —C(O)-alkoxy where alkoxy is as defined herein.

"Alkoxycarbonylalkoxy" refers to a radical —OCR'R"C(O)-alkoxy where alkoxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —OCH$_2$C(O)OCH$_3$, —OCH$_2$C(O)OCH$_2$CH$_3$, —OCH(CH$_3$)C(O)OCH$_2$CH$_3$, —OCH(C$_6$H$_5$)C(O)OCH$_2$CH$_3$, —OCH(CH$_2$C$_6$H$_5$)C(O)OCH$_2$CH$_3$, —OC(CH$_3$)(CH$_3$)C(O)OCH$_2$CH$_3$, and the like.

"Alkoxycarbonylalkylamino" refers to a radical —NRCR'R"C(O)-alkoxy where alkoxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —NHCH$_2$C(O)OCH$_3$, —N(CH$_3$)CH$_2$C(O)OCH$_2$CH$_3$, —NHCH(CH$_3$)C(O)OCH$_2$CH$_3$, —NHCH(C$_6$H$_5$)C(O)OCH$_2$CH$_3$, —NHCH(CH$_2$C$_6$H$_5$)C(O)OCH$_2$CH$_3$, —NHC(CH$_3$)(CH$_3$)C(O)OCH$_2$CH$_3$, and the like.

"Alkylsulfonyl" refers to a radical —S(O)$_2$R where R is an alkyl, or cycloalkyl group as defined herein that may be optionally substituted by one or more substituents as defined herein.

Representative examples include, but are not limited to, methylsulfonyl, ethylsulfonyl, propylsulfonyl, butylsulfonyl, and the like.

"Alkylsulfinyl" refers to a radical —S(O)R where R is an alkyl, or cycloalkyl group as defined herein that may be optionally substituted by one or more substituents as defined herein. Representative examples include, but are not limited to, methylsulfinyl, ethylsulfinyl, propylsulfinyl, butylsulfinyl, and the like.

"Alkylthio" refers to a radical —SR where R is an alkyl or cycloalkyl group as defined/herein that may be optionally substituted by one or more substituents as defined herein. Representative examples include, but are not limited to methylthio, ethylthio, propylthio, butylthio, and the like.

"Amide" or "acylamino" refers to a radical —NR'C(O)R", where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, formylamino acetylamino, cyclohexylcarbonylamino, cyclohexylmethylcarbonyl-amino, benzoylamino, benzylcarbonylamino and the like.

"Amino" refers to the radical —NH$_2$.

"Aryl" refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorine, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleidene, pyrene, pyranthrene, rubicene, triphenylene, trinaphthalene, and the like. Preferable, an aryl group comprises from 6 to 20 carbon atoms, more preferably, between 6 to 12 carbon atoms.

"Arylalkyl" refers to an acyclic alkyl in which one of the hydrogen atoms bonded to a carbon atom, typically a terminal or sp$^3$ carbon atom, is replaced with an aryl group. Typically arylalkyl groups include, but not limited to, benzyl, 2-phenylethan-1-yl, naphthylmethyl, 2-naphthylethan-1-yl, naphthobenzyl, 2-naphthophenylethan-1-yl and the like. Preferably, an arylalkyl group is (C$_6$-C$_{30}$)arylalkyl, e.g., the alkyl moiety of the arylalkyl group is (C$_1$-C$_{10}$) and the aryl moiety is (C$_6$-C$_{20}$), more preferably, an arylalkyl group is ($C_6$-$C_{20}$) arylalkyl, e.g., the alkyl moiety of the arylalkyl group is ($C_1$-$C_8$) and the aryl moiety is ($C_6$-$C_{12}$).

"Arylalkoxy" refers to an —O-arylalkyl radical where arylalkyl is as defined herein that may be optionally substituted by one or more substituents as defined herein.

"Arylalkoxycarbonylalkoxy" refers to a radical —OCR'R"C(O)-arylalkoxy where arylalkoxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —OCH$_2$C(O)OCH$_2$C$_6$H$_5$, —OCH(CH$_3$)C(O)OCH$_2$C$_6$H$_5$, —OCH(C$_6$H$_5$)C(O)OCH$_2$C$_6$H$_5$, —OCH(CH$_2$C$_6$H$_5$)C(O)O CH$_2$C$_6$H$_5$, —OC(CH$_3$)(CH$_3$)C(O)OCH$_2$C$_6$H$_5$, and the like.

"Arylalkoxycarbonylalkylamino" refers to a radical —NRCR'R"C(O)-arylalkoxy where arylalkoxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —NHCH$_2$C(O)OCH$_2$C$_6$H$_5$, —N(CH$_3$)CH$_2$C(O)OCH$_2$C$_6$H$_5$, —NHCH(CH$_3$)C(O)OCH$_2$C$_6$H$_5$, —NHCH(C$_6$H$_5$)C(O)OCH$_2$C$_6$H$_5$, —NHCH(CH$_2$C$_6$H$_5$)C(O)OCH$_2$C$_6$H$_5$, —NHC(CH$_3$)(CH$_3$)C(O)OCH$_2$C$_6$H$_5$, and the like.

"Aryloxycarbonyl" refers to radical —C(O)—O-aryl where aryl is defined herein that may be optionally substituted by one or more substituents as defined herein.

"Aryloxycarbonylalkoxy" refers to a radical —OCR'R"C(O)-aryloxy where aryloxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —OCH$_2$C(O)OC$_6$H$_5$, —OCH(CH$_3$)C(O)OC$_6$H$_5$, —OCH(C$_6$H$_5$)C(O)OC$_6$H$_5$, —OCH(CH$_2$C$_6$H$_5$)C(O)OC$_6$H$_5$, —OC(CH$_3$)(CH$_3$)C(O)OC$_6$H$_5$, and the like.

"Aryloxycarbonylalkylamino" refers to a radical —NRCR'R"C(O)-aryloxy where aryloxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —NHCH$_2$C(O)OC$_6$H$_5$, —N(CH$_3$)CH$_2$C(O)OC$_6$H$_5$, —NHCH(CH$_3$)C(O)OC$_6$H$_5$, —NHCH(C$_6$H$_5$)C(O)OC$_6$H$_5$, —NHCH(CH$_2$C$_6$H$_5$)C(O)OC$_6$H$_5$, —NHC(CH$_3$)(CH$_3$)C(O)OC$_6$H$_5$, and the like.

"Carbamoyl" refers to the radical —C(O)NRR where each R group is independently, hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Carbamate" refers to a radical —NR'C(O)OR", where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, methylcarbamate (—NHC(O)OCH$_3$), ethylcarbamate (—NHC(O)OCH$_2$CH$_3$), benzylcarbamate (—NHC(O)OCH$_2$C$_6$H$_5$), and the like.

"Carbonate" refers to a radical —OC(O)OR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, methyl carbonate (—C(O)OCH$_3$), cyclohexyl carbonate (—C(O)OC$_6$H$_{11}$), phenyl carbonate (—C(O)OC$_6$H$_5$), benzyl carbonate (—C(O)OCH$_2$C$_6$H$_5$), and the like.

"Carboxy" means the radical —C(O)OH.

"Cyano" means the radical —CN.

"Cycloalkyl" refers to a substituted or unsubstituted cylic alkyl radical. Typical cycloalkyl groups include, but are not limited to, groups derived from cyclopropane, cyclobutane, cyclopentane, cyclohexane, and the like. In a preferred embodiment, the cycloalkyl group is ($C_3$-$C_{10}$) cycloalkyl, more preferably ($C_3$-$C_7$) cycloalkyl.

"Cycloheteroalkyl" refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Cycloheteroalkoxycarbonyl" refers to a radical —C(O)—OR where R is cycloheteroalkyl as defined herein that may be optionally substituted by one or more substituents as defined herein.

"Dialkylamino" means a radical —NRR' where R and R' independently represent an alkyl or cycloalkyl group as defined herein that may be optionally substituted by one or more substituents as defined herein. Representative examples include, but are not limited to dimethylamino, methylethylamino, di-(1-methylethyl)amino, (cyclohexyl)(methyl)amino, (cyclohexyl)(ethyl)amino, (cyclohexyl)(propyl)amino, and the like.

"Ester" refers to a radical —C(O)OR, where R is alkyl, substituted alkyl, cycloalkyl, substituted cycloalkyl, cycloheteroalkyl, substituted cycloheteroalkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl as defined herein that may be optionally substituted by one or more substituents as defined herein. Representative examples include, but are not limited to, methyl ester (—C(O)OCH$_3$), cyclohexyl ester (—C(O)OC$_6$H$_{11}$), phenyl ester (—C(O)OC$_6$H$_5$), benzyl ester (—C(O)OCH$_2$C$_6$H$_5$), and the like.

"Ether" refers to a radical —OR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Halogen" means fluoro, chloro, bromo, or iodo.

"Heteroaryl" refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-20 membered heteroaryl, with 5-10 membered heteroaryl being particularly preferred. Preferred heteroaryl groups are those derived from thiophene, pyrrole, benzothiophene, benzofuran, indole, pyridine, quinoline, imidazole, oxazole and pyrazine.

"Heteroaryloxycarbonyl" refers to a radical —C(O)—OR where R is heteroaryl as defined that may be optionally substituted by one or more substituents as defined herein.

"Heteroarylalkyl" refers to an acyclic alkyl radical in which one of the hydrogen atoms bonded to a carbon atom, typically a terminal or sp3 carbon atom, is replaced with a heteroaryl group. Preferably, the heteroarylalkyl radical is a 6-30 carbon membered heteroarylalkyl, e.g., the alkyl moiety of the heteroarylalkyl is 1-10 membered and the heteroaryl moiety is a 5-20 membered heteroaryl, more preferably, a 6-20 membered heteroarylalkyl, e.g., the alkyl moiety of the heteroarylalkyl is 1-8 membered and the heteroaryl moiety is a 5-12 membered heteroaryl.

"Hydroxy" means the radical —OH.

"Oxo" means the divalent radical =O.

"Pharmaceutically acceptable" means approved or approvable by a regulatory agency of the Federal or state government or listed in the U.S. Pharmacopoeia or other generally recognized pharmacopoeia for use in animals, and more particularly in humans.

"Pharmaceutically acceptable salt" refers to a salt of a compound of the invention, which is pharmaceutically acceptable and possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentane propionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tertiary butylacetic acid, laurylsulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound of the invention is administered.

"Phosphate" refers to a radical —OP(O)(OR')(OR"), where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Phosphonate" refers to a radical —P(O)(OR')(OR"), where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Preventing" or "Prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Racemate" refers to an equimolar mixture of enantiomers of a chiral molecule.

"Substituted" refers to a group in which one or more hydrogen atoms are each independently replaced with the same or different substituents(s). Typical substituents include, but are not limited to, —X, —$R^{54}$, —$O^-$, =O, —$OR^{54}$, —$SR^{54}$, —S$^-$, =S, —$NR^{54}R^{55}$, =$NR^{54}$, —$CX_3$, —$CF_3$, —CN, —OCN, —SCN, —NO, —$NO_2$, =$N_2$, —$N_3$, —$S(O)_2O^-$, —$S(O)_2OH$, —$S(O)_2R^{54}$, —$OS(O)_2O^{31}$, —$OS(O)_2R^{54}$, —P(O)(O$^-$)$_2$, —P(O)(O$R^{14}$)($O^{31}$), —OP(O)(O$R^{54}$)(O$R^{55}$), —C(O)$R^{54}$, —C(S)$R^{54}$, —C(O)O$R^{54}$, —C(O)N$R^{54}R^{55}$, —C(O)O$^-$, —C(S)O$R^{54}$, —$NR^{56}$C(O)N$R^{54}R^{55}$, —$NR^{56}$C(S)N$R^{54}R^{55}$, —$NR^{57}$C(N$R^{56}$)N$R^{54}R^{55}$, and —C(N$R^{56}$)N$R^{54}R^{55}$, where each X is independently a halogen; each $R^{54}$, $R^{55}$, $R^{56}$ and $R^{57}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —$NR^{58}R^{59}$, —C(O)$R^{58}$ or —$S(O)_2R^{58}$ or optionally $R^{58}$ and $R^{59}$ together with the atom to which they are both attached form a cycloheteroalkyl or substituted cycloheteroalkyl ring; and $R^{58}$ and $R^{59}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl.

"Sulfate" refers to a radical —OS(O)(O)OR, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Sulfonamide" refers to a radical —S(O)(O)NR'R", where R' and R" are independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein or optionally R' and R" together with the atom to which they are both attached form a cycloheteroalkyl or substituted cycloheteroalkyl ring. Representative examples include but not limited to azetidinyl, pyrrolidinyl, piperidinyl, morpholinyl, 4-(NR'")-piperazinyl or imidazolyl group wherein said group may be optionally substituted by one or more substituents as defined herein. R'" hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Sulfonate" refers to a radical —S(O)(O)OR, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Thio" means the radical —SH.

"Thioether" refers to a radical —SR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Treating" or "Treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically (e.g., stabilization of a discernible symptom), physiologically, (e.g., stabilization of a physical parameter), or both.

"Therapeutically effective amount" means the amount of a compound that, when administered to a patient for treating a disease, is sufficient to effect such treatment for the disease. The "therapeutically effective amount" will vary depending on the compound, the disease and is severity and the age, weight, etc., of the patient to be treated, and can be determined by one of skill in the art without undue experimentation.

The present invention is directed to a method for treating pulmonary hypertension.
Compounds Used in the Invention
Compounds of Formula (I) are useful for the present invention:

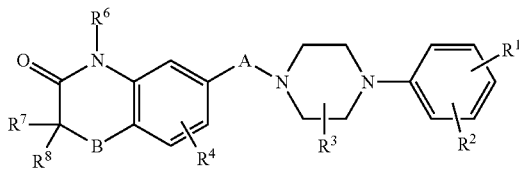

Formula I wherein:
A is $-(CH_2)_n-$, $-O-(CH_2)_n-$, $-S-(CH_2)_n-$, $-S(O)(O)-(CH_2)_n-$, $-NH-(CH_2)_n-$, $-CH_2-O-(CH_2)_n-$, $-(CH_2)_n-O-CH_2-CH_2-$, $-CH_2-S-(CH_2)_n-$, $-(CH_2)_n-S-CH_2-CH_2-$, $-CH_2-S(O)(O)-(CH_2)_n-$, $-(CH_2)_n-S(O)(O)-CH_2-CH_2-$, $-O-C(O)-(CH_2)_n-$, $-S-C(O)-(CH_2)_n-$, $-NH-C(O)-(CH_2)_n-$, $-CH_2-C(O)-O-(CH_2)_n-$, $-CH_2-C(O)-NH-(CH_2)_n-$, $-CH_2-C(O)-S-(CH_2)_n-$, $-(CH_2)_n-C(O)-O-CH_2-CH_2-$, $-(CH_2)_n-C(O)-NH-CH_2-CH_2-$, $-(CH_2)_n-C(O)-S-CH_2-CH_2-$, $-CH_2-O-C(O)-(CH_2)_n-$, $-CH_2-NH-C(O)-(CH_2)_n-$, $-CH_2-S-C(O)-(CH_2)_n-$, $-(CH_2)_n-O-C(O)-CH_2-CH_2-$, $-(CH_2)_n-NH-C(O)-CH_2-CH_2-$, or $-(CH_2)_n-S-C(O)-CH_2-CH_2-$, wherein n is an integer from 1 to 7, preferably n is 2 to 5, for example n is 4;
B is O, S, S(O)(O), or NR$^5$; and
each of R$^1$, R$^2$, R$^3$, R$^4$, R$^5$, R$^6$, R$^7$, and R$^8$ is independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonylalkylamino, alkylsulfinyl, alkylsulfonyl, alkylthio, amino, alkylamino, arylalkylamino, dialkylamino, arylalkoxy, arylalkoxycarbonylalkoxy, arylalkoxycarbonylalkylamino, aryloxycarbonyl, aryloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide, wherein R$^1$, R$^2$, R$^3$, R$^4$, R$^5$, R$^6$, R$^7$ and R$^8$ and A may optionally be substituted with isotopes that include, but not limited to $^2$H (deuterium), $^3$H (tritium), $^{13}$C, $^{36}$Cl, $^{18}$F, $^{15}$N, $^{17}$O, $^{18}$O, $^{31}$P, $^{32}$P, and $^{35}$S; with $^2$H (deuterium) being preferred;
or a pharmaceutically acceptable salt, racemate or diastereomeric mixtures thereof.

In one aspect of the invention, A is $-(CH_2)_n-$.
In another aspect of the invention, A is $-O-(CH_2)_n-$, $-S-(CH_2)_n-$, $-CH_2-O-(CH_2)_n-$, $-(CH_2)_n-O-CH_2-CH_2-$, $-CH_2-S-(CH_2)_n-$, or $-(CH_2)_n-S-CH_2-CH_2-$; with A being $-O-(CH_2)_n-$ preferred.
In another aspect of the invention, A is $-NH-C(O)-(CH_2)_n-$, $-CH_2-NH-C(O)-(CH_2)_n-$, $-CH_2-C(O)-NH-(CH_2)_n-$ or $-(CH_2)_n-C(O)-NH-CH_2-CH_2-$.
In another aspect of the invention, B is O.
In another aspect of the invention, R$^3$, R$^4$, R$^6$, R$^6$, and R$^8$ are H.
In another aspect of the invention, each of R$^1$ and R$^2$ is independently H, halogen (e.g., chloro), haloalkyl, or alkoxy (e.g., methoxy or ethoxy); preferably halogen or alkoxy.
In a preferred embodiment, A is $-O-(CH_2)_n-$, n=2-5; B is O; R$^3$, R$^4$, R$^6$, R$^6$, and R$^8$ are H; and R$^1$ and R$^2$ is independently H, halogen, haloalkyl, or alkoxy.
Preferred compounds of Formula I include, for example,

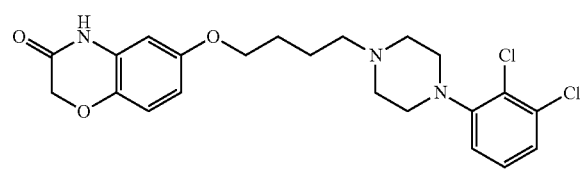 [SMILES: O=C1COc2ccc(OCCCCN3CCN(c4cccc(Cl)c4Cl)CC3)cc2N1]

6-(4-(4-(2,3-dichlorophenyl)piperazin-1-yl)butoxy)-2H-benzo[b][1,4]oxazin-3(4H)-one, and its hydrochloride salt; and

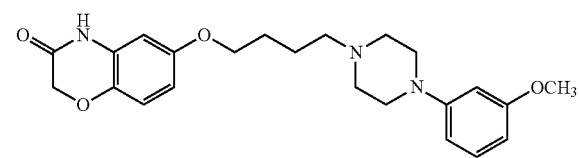 [SMILES: COc1cccc(N2CCN(CCCCOc3ccc4c(c3)NC(=O)CO4)CC2)c1]

6-(4-(4-(2-methoxyphenyl)piperazin-1-yl)butoxy)-2H-benzo[b][1,4]oxazin-3(4H)-one, and its hydrochloride salt.

The compounds useful for the present invention further pertain to enantiomerically isolated compounds of Formula I. The isolated enantiomeric forms of the compounds of Formula I are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. Thus, for example, the compounds are at least about 90% enantiomeric excess, preferably at least about 95% enantiomeric excess, more preferably at least about 97% enantiomeric excess, or even more preferably, at least 99% or greater than 99% enantiomeric excess.

Formula I compounds can be synthesized according U.S. Pat. No. 8,188,076, which is incorporated herewith in its entirety.

Method of Treating Pulmonary Hypertension

The present invention is directed to a method for treating pulmonary hypertension (high blood pressure in the lungs). The method comprises the step of administering an effective amount of a compound of Formula I to a patient who is suffering from pulmonary hypertension. Formula I compounds can lower blood pressure in the pulmonary artery (the blood vessel that leads from the heart to the lungs) of a patient and treat pulmonary arterial hypertention. The treatment can also reduce disease complications, such as shortness of breath, pain crisis, pneumonia, and increase survival.

In one embodiment, the method treats pulmonary hypertsnion in a subject with chronic obstructive pulmonary disease (COPD), with sickle cell disease (SCD), or with human immunodeficiency virus (HIV).

In one embodiment, the method treats depression in patients with pulmonary hypertension. In another embodiment, the method treats anxiety in patients with pulmonary hypertension.

When used to treat pulmonary hypertension, one or more compound of Formula I can be administered alone, or in combination with other agents, to a patient. The patient may be an animal, preferably a mammal, and more preferably a human.

Formula I compounds are preferably administered orally. Formula I compounds may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or composition of the invention. Methods of administration include, but are not limited to, intradermal, intramuscular, intraperitoneal, intravenous, subcutaneous, intranasal, epidural, oral, sublingual, intranasal, intracerebral, intravabinal, transdermal, rectally, by inhalation, or topically, particularly to the ears, nose, eyes or skin. Transdermal administration may be preferred for young children.

Formula I compounds can be delivered via sustained release systems, preferably oral sustained release systems. In one embodiment, a pump may be used (see, Langer, supra; Sefton, 1987, CRC Crit. Ref Biomed. Eng. 14:201; Saudek et al., 1989, N. Engl. J. Med. 321:574).

In one embodiment, polymeric materials can be used (see "Medical Applications of Controlled Release," Langer and Wise (eds.), Wiley, N.Y. (1984); Ranger and Peppas, 1983, J. Macromol. Sci. Rev. Macromol Chem. 23:61; see also Levy et al., 1985, Science 228:190; During et al., 1989, Ann. Neurol. 25:351; Howard et al, 1989, J. Neurosurg. 71:105). In a preferred embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropylmethylcellulose). Other preferred cellulose ethers have been described in the art (Bamba et al., Int. J. Pharm., 1979, 2, 307).

In one embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time controlled release), polymers that are degraded by enzymes (i.e., enzyme controlled release) and polymers that form firm layers that are destroyed by an increase in pressure (i.e., pressure-controlled release).

In still another embodiment, osmotic delivery systems are used for oral sustained release administration (Verma et al., Drug Dev. Ind. Pharm., 2000, 26:695-708). In a preferred embodiment, OROS® osmotic delivery systems are used for oral sustained release delivery devices (See for example, Theeuwes et al., U.S. Pat. No. 3,845,770; and Theeuwes et al, U.S. Pat. No. 3,916,899).

In yet another embodiment, a controlled-release system can be placed in proximity of the target of the compounds and/or composition of the invention, thus requiring only a fraction of the systemic dose (See, e.g., Goodson, in "Medical Applications of Controlled Release," supra, vol. 2, pp. 115-138 (1984)). Other controlled-release systems discussed in Langer, 1990, Science 249:1527-1533 may also be used.

Formula I compounds may be cleaved either chemically and/or enzymatically. One or more enzymes present in the stomach, intestinal lumen, intestinal tissue, blood, liver, brain or any other suitable tissue of a mammal may enzymatically cleave the compounds and/or compositions of the invention.

Pharmaceutical Formulation of the Invention

The present invention is directed to a pharmaceutical formulation for treating pulmonary hypertension. The pharmaceutical formulation contains a therapeutically effective amount of one or more compounds of Formula I, preferably in purified form, together with a suitable amount of a pharmaceutically acceptable vehicle. When administered to a patient, the pharmaceutical formulation is preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present agents, or pH buffering agents. In addition, auxiliary, stabilizing, thickening, lubricating and coloring agents may be used.

Pharmaceutical compositions comprising a compound of the invention may be manufactured by means of conventional mixing, dissolving, granulating, levigating, and emulsifying, encapsulating, entrapping or lyophilizing process. Pharmaceutical compositions may be formulated in conventional manner using one or more physiologically acceptable carriers, diluents, excipients or auxiliaries, which facilitate processing of compounds of the invention into preparations which can be used pharmaceutically. Proper formulation is dependent upon the route of administration chosen.

The present compositions can take the form of solutions, suspensions, emulsion, tablets, pills, pellets, and capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 17$^{th}$ Edition, 1985). Preferred compositions of the invention are formulated for oral delivery, particularly for oral sustained release administration.

Compositions for oral delivery may be in the form of tablets, lozenges, aqueous or oily suspensions, granules, powders, emulsions, capsules, syrups or elixirs, for example. Orally administered compositions may contain one or more optionally agents, for example, sweetening agents such as fructose, aspartame or saccharin; flavoring agents such as peppermint, oil of wintergreen, or cherry coloring agents and preserving agents to provide a pharmaceutically palatable preparation. Moreover, where in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about mM to about 50 mM) etc. Additionally, flavoring agents, preservatives, coloring agents, bile salts, acylcarnitines and the like may be added.

Compositions for administration via other routes may also be contemplated. For buccal administration, the compositions may take the form of tablets, lozenges, etc. formulated in conventional manner. Liquid drug formulations suitable for use with nebulizers and liquid spray devices and EHD aerosol devices will typically include a compound of the invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as alcohol, glycol, polyglycol or fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611). A compound of the invention may also be formulated in rectal or vaginal compositions such as suppositories or retention enemas, e.g., containing conventional suppository bases such as cocoa, butter or other glycerides. In addition to the formulations described previously, a compound of the invention may also be formulated as depot preparation. Such long acting formulations may be administered by implantation (for example, subcutaneously or intramuscularly) or by intramuscular injection. Thus, for example, a compound of the invention may be formulated with suitable polymeric or hydrophobic materials (for example, as an emulsion in an acceptable oil) or ion exchange resins, or as sparingly soluble derivatives, for example, as a sparingly soluble salt.

Dosage for the Treatment

The amount of Formula I compound administered is dependent on, among other factors, the subject being treated, and the weight of the subject, the severity of the affliction, the manner of administration and the judgment of the prescribing physician. For example, the dosage may be delivered in a pharmaceutical composition by a single administration, by multiple applications or controlled release. In one embodiment, the compounds of the invention are delivered by oral sustained release administration. In one embodiment, the compounds of the invention are administered twice per day, and preferably, once per day. Dosing may be repeated intermittently, may be provided alone or in combination with other drugs, and may continue as long as required for effective treatment of the disease state or disorder.

The compounds of Formula I may be administered in the range 0.1 mg to 500 mg, preferably 1 mg to 100 mg per day, such as 5 mg, 10 mg, 15 mg, 20 mg, 25 mg, 35 mg or 50 mg per day, and preferably 10 mg per day.

Combination Therapy

In certain embodiments of the present invention, the compounds of the invention can be used in combination therapy with at least one other therapeutic agent. Formula I compounds and the therapeutic agent can act additively or synergistically. In one embodiment, Formula I compound is administered concurrently with the administration of another therapeutic agent, which can be part of the same composition of Formula I compound. In another embodiment, a composition comprising a compound of the invention is administered prior or subsequent to administration of another therapeutic agent.

The present invention is effective for treating pulmonary hypertension. Compounds of Formula I have potent binding affinity at the serotonin 5-HT2A receptor (compound B, Ki=2.5 nM, see Example 1) and 5-HT2B receptor (compound B, Ki=0.19 nM, see Example 1). In addition, Compounds of Formula I exhibit partial agonist activities for the key subtypes of dopamine (D2) and serotonin (5-HT1A), and antagonist activity at the serotonin 5-HT6 and 5-HT7 receptors. Furthermore, compounds of Formula I (compound B) demonstrated efficacy for PAH in both monocrotoline (MCT) and sugen-hypoxia (SuHx) induced PAH rat models (Example 2 and 3). Compound B attenuates the effects of both MCT and SuHx on the pulmonary vascular tree by decreasing the severity of PAH by decreasing right ventricular hypertrophy (RVH), pulmonary artery pressure, and respiratory resistance.

The invention is illustrated by the following examples.

EXAMPLES

Example 1. In Vitro Pharmacology Results

Two arylpiperazine derivatives of Formula (I) were tested in the in vitro pharmacological assays to evaluate their activities for dopamine, $D_{2S}$, serotonin, $5-HT_{1A}$, $5-HT_{2A}$, $5-HT_{2B}$, $5-HT_6$, and $5-HT_7$ receptors. The in vitro assay protocols and literature references are described herein.

Dopamine, $D_{2S}$ Radioligand Binding Assay

Materials and Methods:

Receptor Source: Human recombinant $D_{2S}$ expressed mammalian cells

Radioligand: [$^3$H]Spiperone (20-60 Ci/mmol) or [3H]-7-hydroxy DPAT, 1.0 nM

Control Compound: Haloperidol or Chlorpromazine
Incubation Conditions: The reactions were carried out in 50 mM TRIS-HCl (pH 7.4) containing 120 mM NaCl, 5 mM KCl, 5 mM MgCl$_2$, 1 mM EDTA for 60 minutes at 25 C. The reaction was terminated by rapid vacuum filtration onto glass fiber filters. Radioactivity trapped onto the filters was determined and compared to control values in order to ascertain any interactions of test compounds with the cloned dopamine—D$_2$ short binding site (Literature Reference: Jarvis, K. R. et al. Journal of Receptor Research 1993, 13(1-4), 573-590; Gundlach, A. L. et al. Life Sciences 1984, 35, 1981-1988.)
Serotonin, 5HT$_{1A}$ radioligand binding assay
Materials and Methods:
Receptor Source: Human recombinant 5-HT$_{1A}$ expressed mammalian cells
Radioligand: [$^3$H]-8-OH-DPAT (221 Ci/mmol)
Control Compound: 8-OH-DPAT
Incubation Conditions: The reactions were carried out in 50 mM TRIS-HCl (pH 7.4) containing 10 mM MgSO$_4$, 0.5 mM EDTA and 0.1% Ascorbic acid at room temperature for 1 hour. The reaction was terminated by rapid vacuum filtration onto glass fiber filters. Radioactivity trapped onto the filters was determined and compared to control values in order to ascertain any interactions of test compounds with the cloned serotonin—5HT$_{1A}$ binding site (Literature Reference: Hoyer, D. et al. Eur. Journal Pharmacol. 1985, 118, 13-23; Schoeffter, P. and Hoyer, D. Naunyn-Schmiedeberg's Arch. Pharmac. 1989, 340, 135-138)
Serotonin, 5HT$_{2A}$ radioligand binding assay
Materials and Methods:
Receptor Source: Human Cortex or Human recombinant 5-HT$_{2A}$ expressed mammalian cells
Radioligand: [$^3$H]-Ketanserin (60-90 Ci/mmol)
Control Compound: Ketanserin
Incubation Conditions: The reactions were carried out in 50 mM TRIS-HCl (pH 7.6) at room temperature for 90 minutes. The reaction was terminated by rapid vacuum filtration onto glass fiber filters. Radioactivity trapped onto the filters was determined and compared to control values in order to ascertain any interactions of test compounds with the serotonin—5HT$_{2A}$ binding site (Literature Reference: Leysen, J. E. et al. Mol. Pharmacol. 1982, 21, 301-314; Martin, G. R. and Humphrey, P. P. A. Neuropharmacol. 1994, 33(3/4), 261-273.) Serotonin, 5HT$_{2B}$ radioligand binding assay
Materials and Methods:
Receptor Source: Human recombinant 5-HT$_{2B}$ expressed CHO-K1 cells
Radioligand: 1.20 nM [3H] Lysergic acid diethylamide (LSD)
Control Compound: Ketanserin
Incubation Conditions: The reactions were carried out in 50 mM TRIS-HCl (pH 7.6) at room temperature for 90 minutes. The reaction was terminated by rapid vacuum filtration onto glass fiber filters. Radioactivity trapped onto the filters was determined and compared to control values in order to ascertain any interactions of test compounds with the serotonin—5HT$_{2B}$ binding site
Serotonin, 5HT$_6$ radioligand binding assay
Materials and Methods:
Receptor Source: Human recombinant 5-HT$_6$ expressed mammalian cells
Radioligand: [1251] SB258585, 15 nM or [$^3$H]LSD, 2 nM
Control Compound: Methiothepin or serotonin
Incubation Conditions: The reactions were carried out in 50 mM TRIS-HCl (pH 7.4) containing 10 mM MgSO$_4$, 0.5 mM EDTA and 0.1% Ascorbic acid at room temperature for 1 hour. The reaction was terminated by rapid vacuum filtration onto glass fiber filters. Radioactivity trapped onto the filters was determined and compared to control values in order to ascertain any interactions of test compounds with the cloned serotonin—5HT$_6$ binding site (Literature Reference: Gonzalo, R., et al., Br. J. Pharmacol., 2006 (148), 1133-1143)
Serotonin, 5HT$_7$ radioligand binding assay
Materials and Methods:
Receptor Source: Human recombinant 5-HT$_7$ expressed CHO cells
Radioligand: [3H] Lysergic acid diethylamide (LSD), 4 nM
Control Compound: Serotonin
Incubation Conditions: The reactions were carried out in 50 mM TRIS-HCl (pH 7.6) at room temperature for 90 minutes. The reaction was terminated by rapid vacuum filtration onto glass fiber filters. Radioactivity trapped onto the filters was determined and compared to control values in order to ascertain any interactions of test compounds with the serotonin—5HT$_7$ binding site The radioligand binding assays were carried out at six to 10 different concentrations and the test concentrations were 0.1 nM, 0.3 nM, 1 nM, 10 nm, 30 nM, 100 nM, 300 nM and 1000 nM.

The in vitro pharmacological activities of the selected compounds A and B using radioligand binding assays are reported in the following table. Compound A=6-(4-(4-(2-methoxyphenyl)piperazin-1-yl)butoxy)-2H-benzo[b][1,4]oxazin-3(-4H)-one hydrochloride. Compound B=6-(4-(4-(2,3-dichlorophenyl)piperazin-1-yl)butoxy)-2H-benzo[b][1,4]oxazin-3(4H)-one hydrochloride.

| Compound | Assay | Ki |
| --- | --- | --- |
| A | D2S | 0.30 nM |
| A | 5-HT1A | 0.65 nM |
| A | 5-HT2A | 118 nM |
| B | D2S | 0.62 nM |
| B | 5-HT1A | 1.50 nM |
| B | 5-HT2A | 2.50 nM |
| B | 5-HT2B | 0.19 nM |
| B | 5-HT6 | 51 nM |
| B | 5-HT7 | 2.70 nM |

Example 2. Evaluation of the Effects of Compound B in the Monocrotoline (MCT) Induced Pulmonary Arterial Hypertension Rat Model The purpose of this study was to assess the effect of the test articles on the monocrotaline-induced pulmonary arterial hypertension (PAH) in rats. The assay was designed to measure the pulmonary and systemic arterial blood pressures in anaesthetized rats with PAH induced by a single subcutaneous dose of monocrotaline. The results of the study are a quantitative measurement of the progression of the disease and its effects on the pulmonary arterial blood pressure (PAP), as well as wet organ weight in rats with induced PAH with and without treatment with test article or reference compound. Furthermore, a detailed morphometric and clinical investigation of the histology of the pulmonary vasculature was performed to correlate vascular remodeling with the functional impact of the onset of the PAH.

Experimental Procedures

Male Wistar-Kyoto rats (Charles River Laboratories) weighing between 200 and 250 grams (approximately 10-12 week-old) were randomized across experimental groups, according to their body weight, with the aim of scheduling one animal per treatment group for each day of terminal surgery (when possible). This resulted in animals from each treatment group being operated on for each surgery day. Rats from treatment groups 2 to 4 received one subcutaneous injection of monocrotaline (MCT) solution (60 mg/kg) in DMSO on Day 0 and were returned to their cages. Rats from control group 1 received one subcutaneous injection of DMSO (vehicle for monocrotaline) on Day 0 and were returned to their respective cages. Treatment with the test article, Compound B (3 mg/kg, 10 mg/kg) b.i.d. in 5% glucose solution, reference compound (sildenafil 50 mg/kg, b.i.d.) or vehicle was initiated and administered starting on Day 0 as scheduled and described in Table 1. Food and water were given ad libitum. Daily observations of the behavior and general health status of the animals were done. Weekly blood draw, body weight and body temperature were taken.

TABLE 1

Treatment Group Assignment and Treatment Information (MCT rat model)

| Gr. # | Group Description | Treatment dose Comp-B | Total Daily dose | Route of Administration | Drug Treatment Duration | Harvest Day | Gr. Size (n) |
|---|---|---|---|---|---|---|---|
| 1 | Control (No MCT) | n/a | n/a | n/a | n/a | Day 28 | 5 |
| 2 | Control-MCT | n/a | n/a | Oral Gavage | n/a | Day 28 | 10 |
| 3 | MCT + Compound B | 3 mg/kg b.i.d | 6 mg/kg | Oral Gavage | Day 0 to Day 27 | Day 28 | 10 |
| 4 | MCT + Compound B | 10 mg/kg b.i.d. | 20 mg/kg | Oral Gavage | Day 0 to Day 27 | Day 28 | 10 |

On the day of surgery, the rats were anaesthetized, instrumented and hemodynamic parameters (systemic arterial blood pressure, right ventricular blood pressure, pulmonary arterial blood pressure, oxygen saturation, respiratory resistance, ventilatory pressure, respiration rate and heart rate) were recorded continuously for 5 minutes or until loss of quality in the pulmonary arterial pressure signal, whichever came first. The recordings included moving the pressure transducer from the right ventricular cavity to the pulmonary artery and back, observing the very clear transitions in diastolic pressures and general pressure waveforms as the catheter entered the artery, and was withdrawn into the ventricle. The rats were then exsanguinated and the pulmonary circulation was flushed with 0.9% NaCl. The trachea, lungs and heart were removed as a whole from the thoracic cavity. The right and left lobes of the lung were weighed before being perfused with 10% NBF and immersed in 10% formalin. The lungs were stored in 10% formalin at room temperature. The heart was excised to measure the wet weights of the right ventricle (RV) and left ventricle including the septum (LV-S) as part of the Fulton index calculation. Arterial blood pressure was recorded continuously throughout the experiment via an intra-arterial fluid-filled catheter (AD Instruments, Colorado Springs, Colo., USA). Diastolic and systolic pressures values were measured in mmHg using cursors readings in the Clampfit 10.2.0.14. Mean arterial blood pressure values were calculated using the following formula:

$$\text{Mean Arterial Pressure} = \text{Diastolic Pressure} + \frac{(\text{Systolic Pressure} - \text{Diastolic Pressure})}{3}$$

Fulton's index was then calculated using the following formula $$\text{Fulton's index} = \frac{\text{right ventricular weight}}{\text{left ventricular} + \text{septum weight}}$$

Values are presented as means±SEM (standard error of the means). Repeat unpaired Student's t-tests were performed in Microsoft Excel 2007 on all experimental conditions, comparing treatment groups to either the control, healthy animals, or the negative control animals (monocrotaline only). Differences were considered significant when p≤0.05. The study results are described in Table 2.

TABLE 2

Effects of Compound B in the monocrotaline (MCT) induced PAH rat model

| Hemodynamic Parameters | MCT + Comp-B 3 mg/kg, bid (n = 9) | MCT + Comp-B 10 mg/kg, bid (n = 9) | Control MCT (n = 9) | Control No MCT (n = 9) |
|---|---|---|---|---|
| Systolic pulmonary pressure (mmHg) | 57.7 | 43.0 | 64.0 | 26.7 |
| Diastolic pulmonary pressure (mmHg) | 19.2 | 14.7 | 21.1 | 11.4 |
| Mean pulmonary pressure (mmHg) | 32.0 | 24.1 | 35.4 | 16.5 |
| Right systolic ventricular pressure (mmHg) | 58.4 | 43.1 | 65.1 | 28.6 |
| Oxygen saturation (%) | 93.5 | 96.5 | 88.5 | 97.4 |
| Respiratory resistance | 15.7 | 10.7 | 20.9 | 11.7 |
| Lung weight (%) | 0.86 | 0.86 | 0.98 | 0.55 |
| Body Weight gain (g) | 22.9 | 23.1 | 7.0 | 64.4 |
| Fulton's index | 0.416 | 0.324 | 0.474 | 0.248 |

Example 3. Evaluation of the Effects of Compound B in the Sugen-hypoxia (SuHx) Induced Pulmonary Arterial Hypertension Rat Model The purpose of this study is to assess the effect of the Compound B (test article) on the Sugen-Hypoxia (SuHx)

induced pulmonary arterial hypertension (PAH) in rats. The assay was designed to measure the pulmonary arterial blood pressures in anaesthetized rats with PAH induced by a single subcutaneous dose of Sugen combined with three weeks in hypoxia. Combined with a macroscopic and morphometric histological examination of the tissues harvested from the animals, the results of the provide a quantitative measurement of the progression of the disease on the systemic arterial blood pressure, pulmonary arterial blood pressure, as well as wet organ weight and vascular remodeling in rats with SuHx-induced PAH treated with test article, vehicle, or reference compound.

Experimental Procedures

Male Wistar-Kyoto rats (Charles River Laboratories) weighing between 200 and 250 grams (approximately 10-12 week-old) were randomized across experimental groups according to their body weight, with the aim of scheduling one rat per treatment group for each day of terminal surgery (when possible). This resulted in animals from each treatment group being operated on for each surgery day. Rats from Groups 2 to 4 (see Table 3) received a single subcutaneous injection of sugen (20 mg/kg) in DMSO on Day 0 and returned to their cages. Rats from Group 1 received one subcutaneous injection of DMSO (vehicle for sugen) on Day 0 and returned to their respective cages. Groups 2-4 were placed in cages for which the controlled air was adjusted to receive a $FiO_2$ equivalent to 0.10 (10%) using a mixture of nitrogen and ambient air controlled by the ventilated cage system. They were kept under these hypoxic conditions for 21 days. While in hypoxia, cages were cleaned and changed every 48 hours, exposing the animals to ambient oxygen levels for less than 5 minutes per cleaning session. The animals were then exposed to ambient oxygen levels from Day 22 to Day 35. Group 1 animals remained in cages exposed to ambient oxygen levels for 35 days. The animals were observed on a daily basis for any changes in their behavior and general health status. Treatment with the test article Compound B (10 mg/kg, 20 mg/kg) b.i.d. in 5% glucose solution, reference compound (sildenafil, 50 mg/kg, b.i.d.) or vehicle was initiated and administered starting on Day 14 as scheduled and described in Table 1. Food and water were given ad libitum. Daily observation of the behavior and general health status of the animals was done. Weekly blood draws and body weights were taken. On the day of surgery, the rats were anaesthetized, instrumented and hemodynamic parameters (systemic arterial blood pressure, right ventricular blood pressure, pulmonary arterial blood pressure, oxygen saturation, respiratory resistance, ventilatory pressure, respiration rate and heart rate) were recorded continuously for 5 minutes or until loss of quality in the pulmonary arterial pressure signal, whichever came first. The recordings included moving the pressure transducer from the right ventricular cavity to the pulmonary artery and back, observing the very clear transitions in diastolic pressures and general pressure waveforms as the catheter entered the artery, and was withdrawn into the ventricle. The rats were then exsanguinated and the pulmonary circulation was flushed with 0.9% NaCl. The trachea, lungs and heart were removed as a whole from the thoracic cavity. The right and left lobes of the lung were weighed before being perfused with 10% NBF and immersed in 10% formalin. The lungs were stored in 10% formalin at room temperature. The heart was excised to measure the wet weights of the right ventricle (RV) and left ventricle including the septum (LV-S) as part of the Fulton index calculation.

TABLE 3

Treatment Group Assignment and Treatment Information (SuHx rat model)

| Gr. # | Group Description | Treatment dose Comp-B | Total Daily dose | Route of Administration | Drug Treatment Duration | Harvest Day | Gr. Size (n) |
|---|---|---|---|---|---|---|---|
| 1 | Control Normoxic | n/a | n/a | n/a | n/a | Day 35 | 5 |
| 2 | Control SuHx | b.i.d | n/a | Oral Gavage | Day 14 to Day 34 | Day 35 | 8 |
| 3 | SuHx + Comp B | 10 mg/kg b.i.d | 20 mg/kg | Oral Gavage | Day 14 to Day 34 | Day 35 | 10 |
| 4 | SuHx + Comp B | 20 mg/kg b.i.d | 40 mg/kg | Oral Gavage | Day 14 to Day 34 | Day 35 | 10 |

Mean arterial blood pressure values and Fulton's index were calculated using the following formula as described above in Example 2. The study results are described in Table 4.

TABLE 4

Effects of Compound B in the sugen-hypoxia (SuHx) induced PAH rat model

| Hemodynamic Parameters | SuHx + Comp-B 10 mg/kg, bid (N = 6) | SuHx + Comp-B 20 mg/kg, bid (N = 6) | Control SuHx (N = 4) | Control Normoxic (N = 4) |
|---|---|---|---|---|
| Systolic pulmonary pressure (mmHg) | 32.2 | 32.0 | 43.0 | 25.0 |
| Diastolic pulmonary pressure (mmHg) | 15.3 | 14.7 | 17.0 | 12.3 |
| Mean pulmonary pressure (mmHg) | 20.9 | 20.4 | 25.7 | 16.5 |
| Right systolic ventricular pressure (mmHg) | 32.8 | 34.2 | 42.8 | 27.0 |
| Oxygen saturation (%) | 95.9 | 96.9 | 93.8 | 95.9 |
| Respiratory resistance | 12.4 | 11.1 | 18.8 | 12.8 |
| Lung weight (%) | 0.65 | 0.62 | 0.71 | 0.49 |
| Body Weight gain (g) | 66.7 | 50.8 | 49.8 | 84.5 |
| Fulton's index | 0.307 | 0.359 | 0.390 | 0.221 |

Example 4. Treatment of Pulmonary Hypertension

Objective: This study examines whether the compound of this invention can lower blood pressure in the pulmonary artery in patients with pulmonary hypertension. The study shows whether the treatment can reduce disease complications, such as shortness of breath, pain crisis, pneumonia, and increase survival.

Patients

Patients are at least 12 years old with sickle cell disease and pulmonary hypertension.

Test Compound: Compound B, 6-(4-(4-(2,3-dichlorophenyl)piperazin-1-yl)butoxy)-2H-benzo[b][1,4]oxazin-3(4H)-one hydrochloride, is formulated in the form of liquid, tablet, or capsule.

Placebo contains the same vehicle without the active compound.

Methodology: This is open-label, 16-week clinical activity study, with Phase A at 6 weeks interim results, and Phase B at 16 week.

A total of 20-120 patients are enrolled; about ¾ of the patients are treated with Compound B, and ¼ of the patients are treated with placebo as adjunctive to standard care.

Patients may have been on steady PAH treatment without satisfactory results. The test compounds and the placebo are delivered either by oral administration or by transdermal patch for 16 weeks.

For oral administration, patients take 0.5-100 mg of test compound or placebo once a day.

For transdermal administration, doses that achieve similar blood concentration as that of effective oral doses are given to patients. The patches are replaced every week, every two weeks, or every 4 week.

Inclusion Criteria:
1. Male or female subjects aged 18-65 years
2. Patients with the following types of pulmonary arterial hypertension (PAH) belonging to WHO Group I:
   Idiopathic (IPAH)
   Heritable (HPAH)
   Associated (APAH) with
      Connective tissue diseases
      Drugs and toxins
3. Patients with PAH in modified NYHA functional class III or IV at the time of enrollment in need of injectable epoprostenol.
4. Patients must be injectable prostanoid treatment-naïve and either
   newly diagnosed and not yet treated with specific PAH therapies or
   currently treated with existing background PAH therapy with one or more of the following medications for 90 days prior to enrollment and on a stable dose for 30 days prior to enrollment:
      Bosentan
      Ambrisentan
      Sildenafil
      Tadalafil
5. Women of childbearing potential must use a reliable method of contraception.

Exclusion Criteria:
1. Patients with respiratory and/or cardiovascular distress in need of emergency care including i.v. epoprostenol administration or any vasopressive i.v. drugs
2. Known pulmonary veno-occlusive disease (PVOD)
3. Current use of i.v. inotropic agents
4. Tachycardia with heart rate >120 beats/min
5. Pulmonary arterial hypertension related to any condition other than those specified in the inclusion criteria
6. Known hypersensitivity to the formulations of ACT-385781A or any of its excipients, and Flolan or any of its excipients
7. Use of inhaled iloprost or treprostinil during the week prior to screening
8. Cerebrovascular events (e.g., transient ischemic attack or stroke) within 6 months of screening
9. History of myocardial infarction
10. History of left-sided heart disease, including any of the following:
    hemodynamically significant aortic or mitral valve disease
    restrictive or congestive cardiomyopathy
    left ventricular ejection fraction <40% by multigated radionucleotide angiogram(MUGA), angiography, or echocardiography
    unstable angina pectoris
    life-threatening cardiac arrhythmias
11. Chronic bleeding disorder
12. Infection(s) within the past month that in the mind of the investigator would contraindicate the use of epoprostenol
13. Pregnancy or breast-feeding
14. Participation in another clinical trial, except observational (noninterventional), or receipt of an investigational product within 30 days prior to randomization
15. Any known factor or disease that might interfere with treatment compliance, study conduct or interpretation of the results such as drug or alcohol dependence or psychiatric disease
16. Known concomitant life-threatening disease other than PAH with a life expectancy <12 months Primary Outcome Phase A (6 Week) Pulmonary Vascular Resistance Phase B (16 Week) Functional Improvement Baseline Study Before starting treatment, patients have baseline studies, including a pregnancy test for females of childbearing age; a chest x-ray; pulmonary function tests to measure how much air the patient can breathe in and out; an echocardiogram (heart ultrasound); a 6-minute walk test to measure exercise capacity; a quality-of-life assessment and a pain inventory. Patients undergo heart catheterization to evaluate the severity of hypertension before beginning the treatment.

Criteria for Evaluation:

During treatment, patients are monitored with the following:
   Heart catheterization follow-up: week 6 Echocardiogram: weeks 6 and 16.
   6-minute walk test: weeks 6, 10 and 16.
   Measurements of weight, blood pressure and heart rate: weeks 6, 10 and 16.
   Pregnancy test for women of childbearing age: weeks 6, 10 and 16.
   Pain questionnaire once a day for a week: weeks 6 and 10
   Quality-of-life questionnaire: week 6 and 16.
   Anxiety depression and cognitive battery at weeks 6 and 16
   Biomarker changes, as inflammation including cytokines as interleukins While the invention has been particularly shown and described with reference to a preferred embodiment and various alternate embodiments, it will be understood by persons skilled in the relevant art that various changes in form and details can be made therein without departing from the scope of the invention. All printed patents and publications referred to in this application are hereby incorporated herein in their entirety by this reference.

What is claimed is:

1. A method of treating pulmonary hypertension in a subject, the method comprising administering to a subject suffering from pulmonary hypertension an effective amount of a compound of:

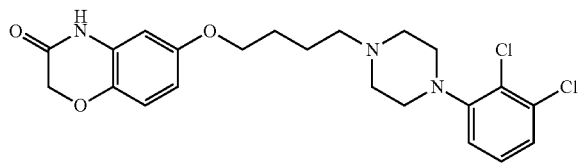 [SMILES: O=C1COc2ccc(OCCCCN3CCN(c4cccc(Cl)c4Cl)CC3)cc2N1]

or a pharmaceutically acceptable salt thereof.

2. The method according to claim 1, wherein the compound is in the form of a hydrochloride salt.

3. The method according to claim 1, wherein the compound is administered in a pharmaceutical composition comprising a pharmaceutically acceptable carrier, excipient, or diluent.

4. The method according to claim 1, wherein the compound is orally administered.

5. The method according to claim 1, which treats pulmonary arterial hypertension.

6. The method according to claim 1, which treats pulmonary hypertension in a subject with chronic obstructive pulmonary disease (COPD).

7. The method according to claim 1, which treats pulmonary hypertension in a subject with sickle cell disease.

8. The method according to claim 1, which treats pulmonary hypertension in a subject with human immunodeficiency virus (HIV).

9. The method according to claim 1, which further treats depression in the subject.

10. The method according to claim 1, which further treats anxiety in the subject.

* * * * *